(12) United States Patent
Arai et al.

(10) Patent No.: US 10,359,394 B2
(45) Date of Patent: Jul. 23, 2019

(54) CAPILLARY ELECTROPHORESIS DEVICE AND CAPILLARY CASSETTE USING THE SAME

(71) Applicant: SHIMADZU CORPORATION, Kyoto-shi, Kyoto (JP)

(72) Inventors: Akihiro Arai, Kyoto (JP); Taigo Nishida, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 111 days.

(21) Appl. No.: 15/632,798

(22) Filed: Jun. 26, 2017

(65) Prior Publication Data

US 2018/0372681 A1 Dec. 27, 2018

(51) Int. Cl.
*G01N 27/453* (2006.01)
*G01N 27/447* (2006.01)
*G01N 21/64* (2006.01)
*G01N 21/03* (2006.01)

(52) U.S. Cl.
CPC ......... *G01N 27/44721* (2013.01); *G01N 2021/0346* (2013.01); *G01N 2021/6417* (2013.01); *G01N 2021/6482* (2013.01)

(58) Field of Classification Search
CPC ............ G01N 27/44717; G01N 27/44782
See application file for complete search history.

(56) References Cited

U.S. PATENT DOCUMENTS 5,757,014 A * 5/1998 Bruno ............ G01N 21/645
250/458.1
6,780,300 B1 * 8/2004 Alberto ........... G01N 27/44708
204/601

FOREIGN PATENT DOCUMENTS

JP  2004-532384 A  10/2004
JP  2012-098309 A   5/2012

OTHER PUBLICATIONS

Nikcevic et al., "Parallel separations using capillary electrophoresis on a multilane microchip with multiplexed laser induced fluorescence detection," Electrophoresis Aug. 2010; 31(16): 2796-2803 (Year: 2010).*

* cited by examiner

*Primary Examiner* — Alexander S Noguerola
(74) *Attorney, Agent, or Firm* — Sughrue Mion, PLLC

(57) ABSTRACT

In a capillary electrophoresis device, detection window sections of a plurality of capillaries are arranged, and a capillary cassette is mounted and used, the capillary cassette having an excitation-side positioning part and a fluorescence-side positioning part so as to hold the detection window section array therebetween. The capillary electrophoresis device includes an excitation optical system unit and a fluorescence-receiving unit having positioning parts positioned to the capillary cassette. The excitation optical system unit includes a rod-like lens array configured to irradiate an excitation light to each detection window section. The fluorescence-receiving unit includes a rod-like lens array configured to receive a fluorescence from each detection window section, and an optical fiber for each rod-like lens configured to guide fluorescence from the rod-like lens to a detector side.

14 Claims, 6 Drawing Sheets

CAPILLARY ELECTROPHORESIS DEVICE AND CAPILLARY CASSETTE USING THE SAME

TECHNICAL FIELD

The present invention relates to capillary electrophoresis devices used as DNA base sequence analyzers and analyzers used in other biochemistry fields; in particular, the present invention relates to multicapillary electrophoresis devices, and capillary cassettes used as consumable goods in such capillary electrophoresis devices.

BACKGROUND ART

A multicapillary electrophoresis device using a laser as the excitation light source and used for detecting fluorescence, typified by a DNA sequencer, has high reliability in producing analysis results; therefore, it is still widely used even now in the era when a base sequence analysis device with a markedly high throughput like a next-generation sequencer has permeated. Equipment used for the purpose of analyzing genes other than a DNA sequencer are required to have even higher separability and high sensitivity.

On the one hand, the equipment for processing many samples at high sensitivity and a high throughput needs a huge optical system and precise and expensive capillary cassettes. On the other hand, in the equipment for processing a comparatively small number of samples, there is no equipment with a detection optical system configured to be compact and have high sensitivity and a low capillary cost.

The capillary cassette used in a multicapillary electrophoresis device needs to be changed to a new one since the cassette is a consumable good whose characteristics unavoidably changed over time. When a capillary cassette is mounted to a multicapillary electrophoresis device, a relative alignment of the capillary center in a detection section and an optical system must be realized while maintaining convenience for a user.

As an electrophoresis device of a system in which a capillary cassette is exchanged, the following capillary electrophoresis device has been proposed: a capillary array is supported by a resin (plastic) frame, and a holding part of a sample injection end, a capillary bending part, a detection part, and an injection end holding part of a separation medium are fixed according to a predetermined procedure, respectively (see Patent Literature 1).

A multichannel cartridge easily replaced as a unified cartridge structure containing optical elements and a reagent reservoir in which the alignment has been carried out in advance has also been proposed as another system of a capillary cassette (see Patent Literature 2).

PRIOR ART LITERATURES

Patent Literatures

[Patent Literature 1] Japanese Unexamined Patent Application Publication No. 2012-098309
[Patent Literature 2] Published Japanese Translation of a PCT Application No. 2004-532384

SUMMARY OF INVENTION

Problem to be Solved by the Invention

Those using a resin (plastic) frame, as described in Patent Literature 1, are not necessarily easy to handle, and a careful treatment is required in order to prevent breakage to and obtain predetermined performances of a capillary. Furthermore, those with cartridges including optical elements, or the like, as described in Patent Literature 2, are expensive in terms of cost, although it is easy to handle.

The present invention aims to provide a multicapillary electrophoresis device that allows an easy operation for obtaining predetermined performances and a capillary cassette that can be replaced easily and manufactured at low cost.

Means for Solving the Problems

The capillary electrophoresis device of the present invention has detection window sections of a plurality of capillaries arranged and uses capillary cassettes having an excitation-side positioning part and a fluorescence-side positioning part on both sides of the detection window array. The device is configured so that such capillary cassette is attached to a cassette loading device and positioned with respect to an excitation optical system unit and a fluorescence-receiving unit.

An excitation optical system unit has a positioning part positioned at the excitation-side positioning part of the capillary cassette attached to the cassette loading device and has an excitation light irradiation section containing a rod-like lens array that has an array corresponding to the detection window array so that the excitation light is irradiated to each of the detection window section of a capillary cassette.

A fluorescence-receiving unit has a positioning part positioned at the fluorescence-side positioning part of the capillary cassette attached to the cassette loading device and has the fluorescence-receiving part containing a rod-like lens array that has the array corresponding to the detection window array so as to allow reception of fluorescence from each of the detection window section of a capillary cassette.

The excitation optical system unit and the fluorescence-receiving unit are not built into the capillary cassette as one unit, but provided removably to the capillary cassette. This point is different from the cartridge disclosed in Patent Literature 2.

The capillary cassette of the present invention has detection window sections of the plurality of capillaries arranged, a positioning part on the excitation side and the fluorescence side on both sides of the detection window array, and is used in the capillary electrophoresis device of the present invention. And the capillary cassette is equipped with a cassette housing, wherein a plurality of capillaries are arranged between one end and the other end of that cassette housing, and the positioning part of this capillary cassette is configured by that cassette housing.

Effect of the Invention

The capillary electrophoresis device of the present invention includes a rod-like lens array with the array corresponding to the detection window array so as to allow the excitation optical system unit to irradiate an excitation light to each of the detection window section of a capillary cassette; therefore, compared to the configuration in which a line beam is directly irradiated to a capillary, the device of the present invention has high excitation light density; therefore, the light can be extracted with maximum excitation efficiency.

If there is only few numbers of capillaries contained in a capillary cassette, the rod-like lens array also has an advantage of being able to constitute a small irradiation optical system or receiving optical system.

Because the capillary cassette of the present invention has a positioning part on the excitation side and the fluorescence side on both sides of the detection window section of a capillary in the cassette housing in which capillaries have been arranged, the optical axis can be adjusted at high accuracy simply by positioning and attaching a capillary cassette to an excitation optical system unit and a fluorescence-receiving unit, and the attachment of the capillary cassette can be performed with ease.

Devising a cassette housing to serve as the positioning part of the capillary cassette allows a capillary cassette to be made into smaller size and is also effective in low cost production.

And since the capillary cassette also does not include any optical element of an excitation optical system or any element of a fluorescent optical system, the manufacturing cost of the capillary cassette, which is a consumable good, can be kept low.

Thus, the capillary electrophoresis device of the present invention can be used, for example, as a small-scale DNA sequencer, and can also meet the demands for other purposes, so it is possible to realize a measurement device that is small in size, high in sensitivity, and low in cost, including the cost of the consumable goods.

DESCRIPTION OF EXEMPLARY EMBODIMENTS

Figure 1:
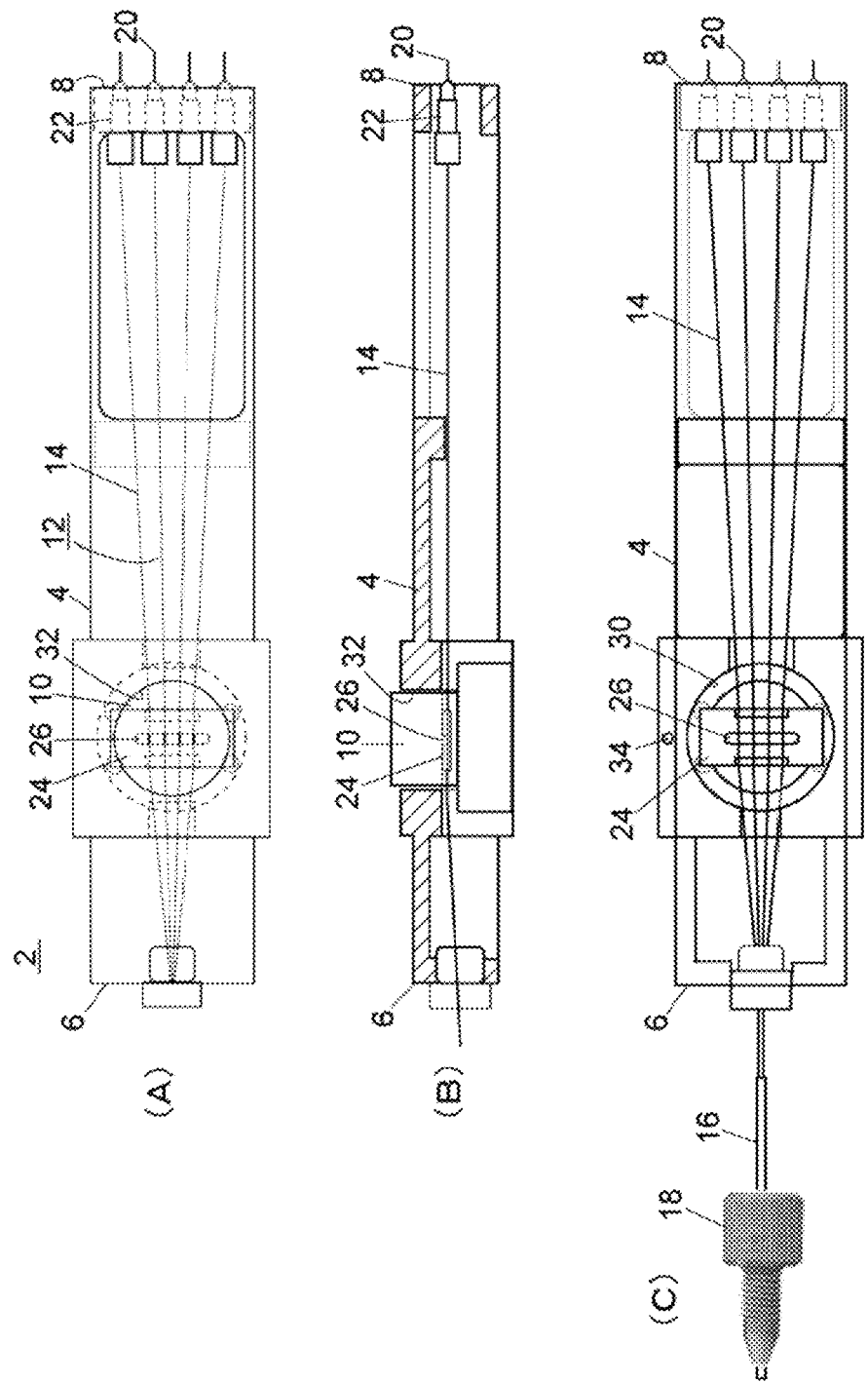
FIG. 1 is a drawing illustrating the first example of embodiment of a capillary cassette, wherein (A) is a plan view, (B) is a cross sectional view along the longitudinal direction, and (C) is a bottom view.
Figure 2:
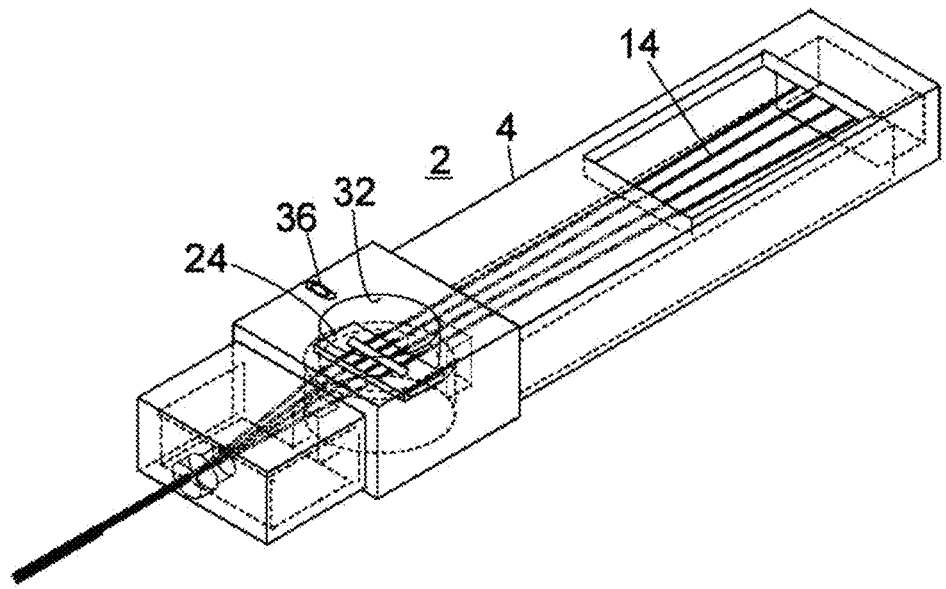
FIG. 2 is a perspective view of the same example of embodiment.

A cassette loading device can be provided with a temperature control mechanism for adjusting the temperature of the capillaries in the capillary cassette mounted in the embodiment of the present invention. The temperature of a capillary array can be distributed uniformly and promptly by the temperature control mechanism, and changes of signals over time can be suppressed.

Although a fluorescence from a rod-like lens of a fluorescence-receiving unit may be received directly with a detector, optical fibers having an end surface for light incidence and for guiding the incidence fluorescence to the detector side may also be provided for each rod-like lens at the position where a fluorescence from a rod-like lens is received. The fluorescence-receiving unit provided with such optical fibers has an advantage in that it cannot be easily influenced by a stray light, or the like, since the optical fibers arranged in the latter stage of a rod-like lens act as a pinhole.

It may also be reconstructed so that the end surfaces on the detector side of all the optical fibers may gather in a narrow region. In this case, when the detector is provided with a spectroscope, the aberration due to an imperfect alignment in a spectroscope can be reduced.

A cathode block that connects the tip of a capillary to a flow path for sample suction or application of electrophoretic voltage can also be provided on the anode-side end of the capillary cassette attached to the cassette loading device.

The excitation optical system unit contains a rod-like lens array, so it is possible to have high excitation light density and improve excitation efficiency; thereby, an excitation light optical system may be made as a multiunit arranged in parallel. In one embodiment, a cassette loading device has a configuration in which a plurality of capillary cassettes can be mounted, and an excitation optical system unit is equipped with a common excitation light source, an excitation light irradiation section for every capillary cassette, and an optical-path switching mechanism in which the optical path of the excitation light from the excitation light source is switched to lead the excitation light to any of the excitation light irradiation section; and a fluorescence-receiving unit can be configured so as to be arranged for every capillary cassette.

By switching an optical path, an electrophoresis separation can be detected in one capillary cassette, while pretreatments including washing a flow path, filling a separation buffer, etc. can be performs alternately in parallel in the other capillary cassette, and as a result, it is possible to improve the throughput thereof.

There may be a configuration in which another excitation light source is used for each capillary cassette, or the fluorescence detection intensity may be changed for each capillary cassette according to the variations in the light source intensity of the excitation light source; however, using the common excitation light source as in this embodiment eliminates the problem caused by the variations in the light source intensity of the excitation light source.

The entire capillary electrophoresis device can be made small since only one excitation light source is used, and the cost can also be kept low.

A GRIN lens, a spherical/aspheric lens, or a lens array can be used as the rod-like lens.

The excitation optical system unit can be provided with a group of Powell lenses or an aspherical lenses arranged towards the direction in which the excitation light from the excitation light source is converted to a line-shaped beam in alignment with the rod-like lens array.

The capillary cassette in one embodiment is further provided with a substrate having a section having a trench in a V shape at equal intervals, wherein an array of detection window sections is configured where a plurality of capillaries is arranged one at a time in one trench of the above-mentioned substrate. Since the outer shape of a capillary is cylindrical, the trench in a V shape makes it easy to position and hold a capillary to a predetermined position.

The first example of embodiment of a capillary cassette will be described with reference of FIG. 1 to FIG. 4.

The capillary cassette 2 has a detection area 10 through which the light for measurement penetrates at the position between the one end 6 and the other end 8 of the cassette housing 4. The cassette housing 4 is made of resin (plastic) and manufactured by molding or machining.

The capillary bundle 12 contains a plurality of capillaries 14. The number of the capillaries 14 contained in the capillary bundle 12 is not particularly limited; the number can be set to, for example, 4 or 8 depending on the number of samples to be analyzed at once. In this example of embodiment, an explanation will be given assuming that the number of the capillaries 14 contained in the capillary bundle 12 is set to four. The capillaries 14 are arranged over the both ends of the cassette housing 4.

The ends (the left-hand side in FIG. 1) of all the capillaries 14 included in the capillary bundle 12 are bundled to one, wherein a bundle processing is carried out by allowing [those capillary ends] to protrude from the end 6 of the cassette housing 4, to pass through a tube 16 made of heat resistant resin, for example, PEEK (polyether ether ketone), and to be adhered with a heat-resistant epoxy resin adhesive. The fitting 18 for the connection with a flow path is attached to one end of the capillary bundle 12 to which the bundle processing has been performed.

The other ends 20 of the capillaries 14 contained in the capillary bundle 12 are perpendicularly cut in the length direction of the capillaries 14 so as to be able to merge with the flow path 62 (refer to FIG. 5.), when inserted into a cathode block 60, which will be mentioned below. The fitting 22 is mounted to the other end side of each capillary 14 in order to fix it to the other end 8 of the cassette housing 4. The other ends 20 of the capillaries 14 are fixed to the cathode block 60 by the fittings 22.

Although the capillary 14 is not particularly limited, for example, the outer diameter may be in the range of from 186 ±6 to 363 ±10 μm, the inner diameter may be 50 ±3 μm, and the overall length may be 145 mm, and the effective length from the other end 20 to the detection window section 14A may be 85 mm. The size of the tube 16 is not particularly limited either, for example, the outer diameter may be 1.6 mm and an inner diameter may be in the range of from 0.75 to 1.0 mm.

The capillary array substrate 24 is fixed to the detection area 10 by an adhesive. The capillary array substrate 24 has an opening 26 that allows transmission of a light to be measured, wherein all capillaries 14 contained in the capillary bundle 12 are arranged at equal intervals in the opening 26.

Figure 4:
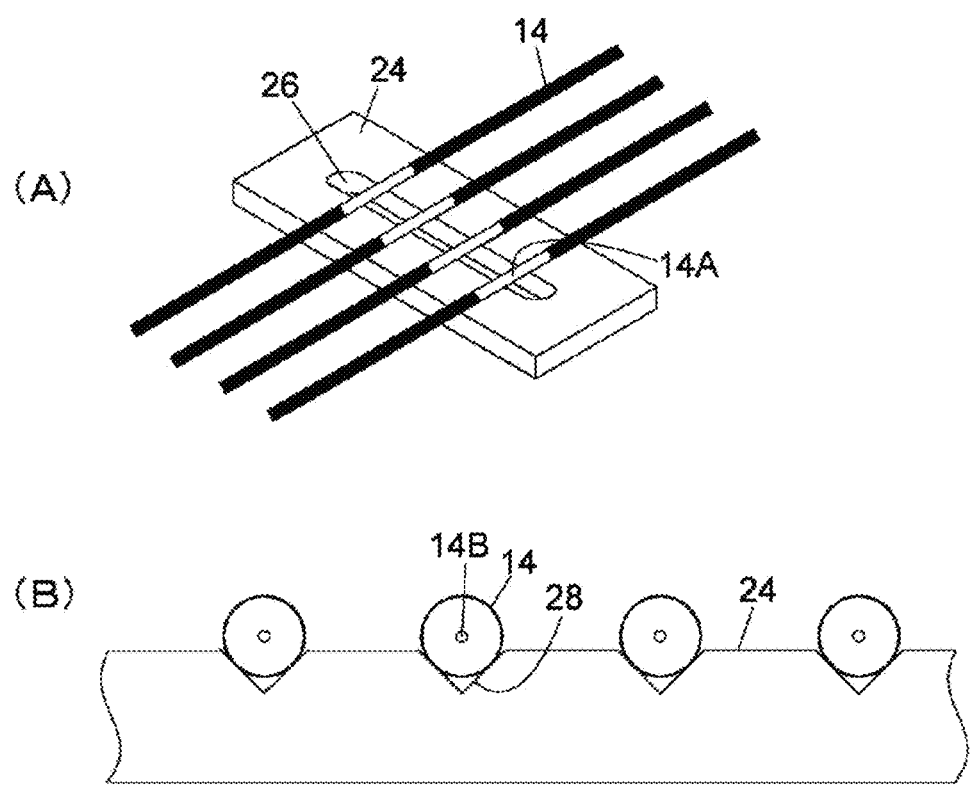
FIG. 4 is a drawing illustrating the state of the capillary being fixed to the capillary array substrate in the same example of embodiment, wherein (A) is a perspective view and (B) is a cross sectional view along the V groove array of the capillary array substrate.

An example of the capillary array substrate 24 is shown in FIG. 4. The opening 26 is a slit 1 mm wide, for example, and V grooves 28 are arranged at equal intervals in the longitudinal direction of the opening 26 at the capillary array substrate 24. The direction of V groove 28 is a direction in which the capillaries 14 cross the opening 26, after the capillaries 14 are inserted into the V grooves 28. By inserting the capillaries 14 into the V grooves 28 one at a time and fixing it to the substrate 24 with an adhesive, the capillaries 14 are arranged at equal intervals and fixed to the capillary array substrate 24.

The capillary 14 is a capillary tube made of quartz covered with resin for protection. In the capillary 14, the portion crossing the opening 26 has its resin coating for protection removed to expose the capillary tube and serves as the detection window section 14A. An excitation light is irradiated to the detection window section 14A as a light to be measured, and the fluorescence emitted from the sample that passes through the inside of the inner diameter 14B of the capillary 14 is emitted from the detection window section 14A. Since the position where the excitation light is irradiated at the detection window section 14A is in the opening 26, the scattering of excitation light or fluorescence between the V grooves 28 and the capillaries 14 is avoided.

To continue the explanation by returning to FIG. 1, the positioning parts 30 and 32 for positioning the excitation optical system unit and the fluorescence-receiving unit of an electrophoresis apparatus to both the upper and lower sides of the capillary array substrate 24 are provided to the detector 10 of the capillary cassette 2. The positioning parts 30 and 32 are configured by the openings of the cassette housing 4 itself in the capillary cassette 2 of this example of embodiment.

The positioning part 30 is provided below the capillary cassette 2, and in order to position an excitation optical system unit from below the capillary cassette 2, the positioning part 30 serves as an opening in a cylindrical shape or a shape of a truncated cone where the side surface is slightly tilted corresponding to the shape of the end surface of the excitation light irradiation section. In order to secure the end surface of the excitation light irradiation section inserted into the opening of the positioning part 30 so as not to circumferentially rotate the opening of the positioning part 30, a hole 34 is opened in the back surface of the capillary cassette 2, and the relative rotation with the capillary cassette 2 and the excitation optical system unit is prevented by inserting the pin 80 of the end surface of the excitation light irradiation section, which will be mentioned below, into the hole 34.

The positioning part 32 is provided above the capillary cassette 2, and in order to position a fluorescence-receiving unit above the capillary cassette 2, the positioning part 32 serves as an opening in a cylindrical shape or in a shape of truncated cone in which the side surface is slightly tilted corresponding to the shape of the end surface of the fluorescence-receiving unit. In order to secure the end surface of the fluorescence-receiving unit inserted into the opening of the positioning part 32 so as not to circumferentially rotate the opening of the positioning part 32, a hole 36 is opened in the surface of the capillary cassette 2, and the relative rotation with the capillary cassette 2 and the fluorescence-receiving unit is prevented by inserting the pin 84 of the end surface of the fluorescence-receiving unit, which will be mentioned below, into the hole 36 (refer to FIG. 2.).

The capillary array substrate 24 has a medial axis perpendicular to the substrate surface, and the cylindrical or truncated cone-shaped openings of the positioning parts 30 and 32 also have medial axes. The capillary array substrate 24 is fixed to the cassette housing 4 so as to correspond to those medial axes.

Figure 3:
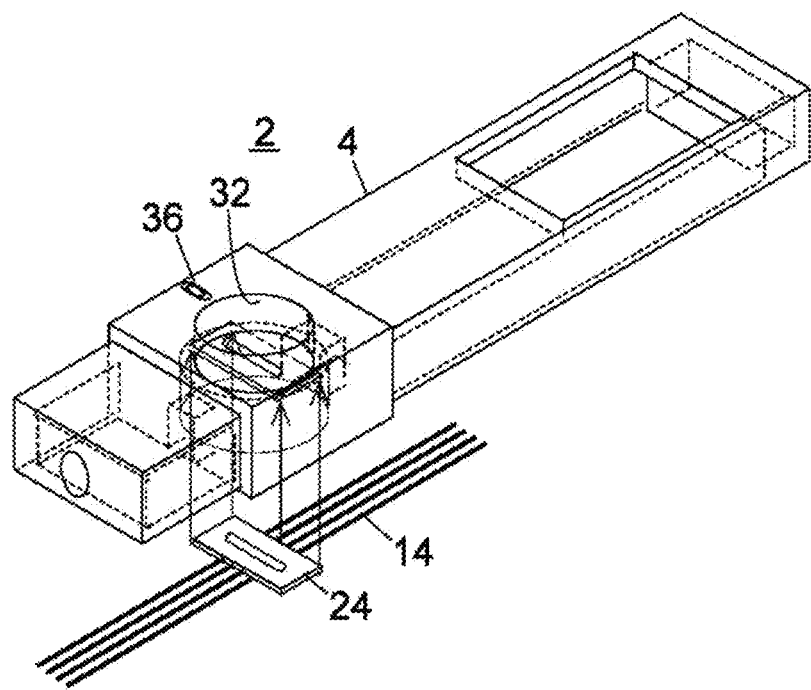
FIG. 3 is an exploded perspective view of the same example of embodiment.

When the side on which V grooves 28 are provided is made to serve as the surface side of the capillary array substrate 24 shown in FIG. 4, the back surface side of the capillary array substrate 24 is secured so as to abut the back surface side of the cassette housing 4 as shown in FIG. 3. As shown in FIG. 1 at (B) and FIG. 3, when the capillary array substrate 24 is secured to the cassette housing 4, the surface side of the capillary array substrate 24 turns towards the back surface side of the cassette housing 4, wherein capillaries 14 are arranged via the capillary array substrate 24 at the back surface side of the cassette housing 4.

Figure 5:
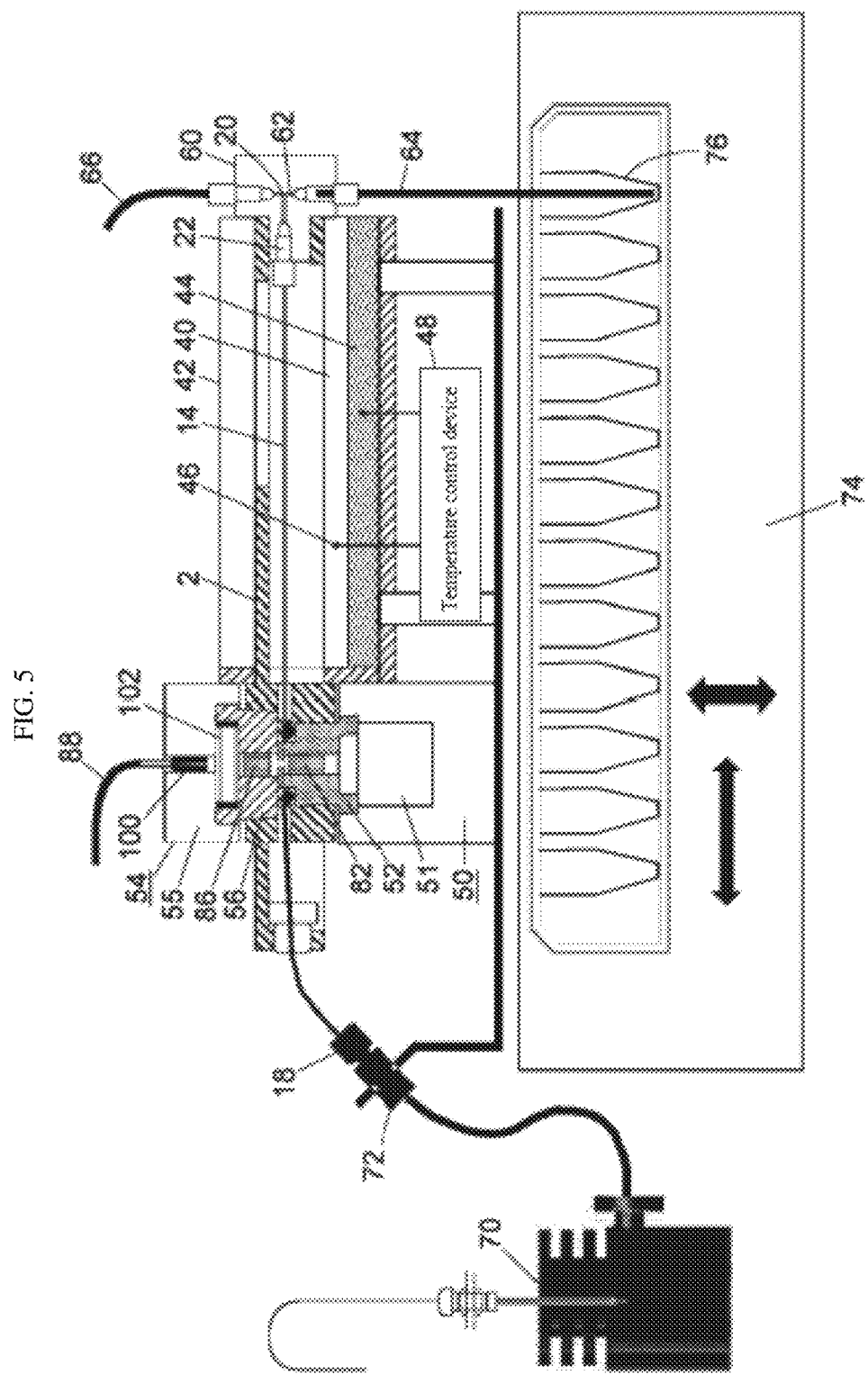
FIG. 5 is a schematic configuration diagram showing a multicapillary electrophoresis device of one example of embodiment in the state where the capillary cassette of one example of embodiment is mounted.

FIG. 5 represents a multicapillary electrophoresis device of one example of embodiment in the state where the capillary cassette 2 of one example of embodiment is mounted.

The mounting device equipped with the capillary cassette 2 comprises a mounting base 40 consisting of an aluminum block whose top surface can be opened and for holding the capillary cassette 2 placed horizontally thereon, and a lid 42 for covering the capillary cassette 2 in a sealed state while the capillary cassette 2 is placed on the mounting base 40.

The mounting base 40 constitutes a part of temperature control mechanism along with the heat block 44 in contact with and arranged on the lower surface. A temperature sensor 46 is attached to the mounting base 40, the temperature controller 48 incorporates a detection signal from the temperature sensor 46 and controls the energization to the heater built into the heat block 44 so that the temperature of the mounting base 40 stays at a predetermined temperature. The lid 42 is covered with thermal insulation for the purpose of preventing the capillaries 14 in the capillary cassette 2 from being affected by external temperature changes. The temperature controller 48 may be configured singly, or it may be realized by a computer for controlling the operation of a multicapillary electrophoresis device.

The excitation optical system unit 50 is fixed under the capillary cassette 2, while the capillary cassette 2 is being placed on the mounting base 40, so that the fluorescence-receiving unit 54 can be arranged from above the capillary cassette 2.

The excitation light irradiation section 51 of the excitation optical system unit 50 is equipped with a lens holder 52 at the end surface. The lens holder 52 is in a cylindrical shape or a shape of a truncated cone with a side surface slightly tilted and inserted in the positioning part 30 for the excitation optical system unit of the capillary cassette 2. The capillary cassette 2 is placed on the mounting base 40 and fixed to the position where the lens holder 52 is inserted into the positioning part 30.

The rod lens 82 that condenses and irradiates an excitation light to the capillaries 14 is arranged in the lens holder 52.

The fluorescence-receiving unit 54 is equipped with a lens holder 56 at the end surface of the fluorescence-receiving unit 55. The lens holder 56 is in a cylindrical shape or a shape of truncated cone whose side is slightly tilted, wherein this holder is inserted into the positioning part 32 for the fluorescence-receiving unit of the capillary cassette 2 placed on the mounting base 40.

Rod lenses 86 at the position where the fluorescence emitted from the sample passing through the inside of the capillaries 14 is received are arranged in the lens holder 56. The rod lenses 86 condense and emit the light received. Connectors 100 for holding the end surfaces of the optical fibers 88 are provided at the positions where the light emitted from the rod lenses 86 is received. The connectors 100 hold the cores of the ends of the optical fibers 88, and the tip surfaces of the optical fibers 88 are positioned at the condensed position of the light emitted from the rod lenses 86. Since the tip surfaces of the optical fibers 88 positioned by the connectors 100 act as pinholes, the structure in the lens holder 56 by such connectors 100 cannot be easily influenced by a stray light, or the like.

Fluorescence filters 102 are disposed between the rod lenses 86 and the end surfaces of the optical fibers 88 held by the connectors 100. These fluorescence filters 102 remove the excitation light irradiated from the rod lenses 82 in the lens holder 52 of the excitation optical system unit and have wavelength characteristics that allow penetration of the fluorescence from the samples that pass through the capillaries 14. Not only can the fluorescence filters 102 be arranged in the lens holder 56 in this manner but the filters can also be arranged on the detector side, such as image elements to which the tips of the optical fibers 88 are led.

A cathode block 60 is provided to the mounting base 40 at the other end 20 of the capillary 14 in the state where the capillary cassette 2 is being placed on the mounting base 40. The flow path 62 in the vertical direction for sample suction or application of electrophoretic voltage is provided in the cathode block 60, wherein one end of the flow path 62 is connected to the flow path 64 immersed in a sample, a buffer solution, or a washing liquid, and the other end is connected to the flow path 66 for suction. A horizontal hole into which the other end 20 of the capillary 14 is inserted and connected to the flow path 62 is also provided in the cathode block 60. When the capillary cassette 2 is placed on the mounting base 40, the capillaries 14 are connected to the flow path 62 by inserting the other end 20 of the capillaries 14 into the hole of the cathode block 60. The cathode block 60 may be arranged individually for each capillary 14, or only the number of the capillaries included in a capillary bundle may be connected integrally.

The fitting 18 of the one end side of the capillary 14 in the state where the capillary cassette 2 is being placed on the mounting base 40 is fixed to the connection part 72 connected to the anode reservoir 70.

An autosampler 74 is arranged under the cathode block 60, and cuvettes 76 containing a sample, a buffer liquid, or a washing liquid are stored in the autosampler 74. When the autosampler 74 moves the cuvettes 76 to the horizontal direction and the vertical direction, the tip of the flow path 64 is dipped in the cuvette 76 containing a sample, a buffer liquid, or a washing liquid.

Figure 6:
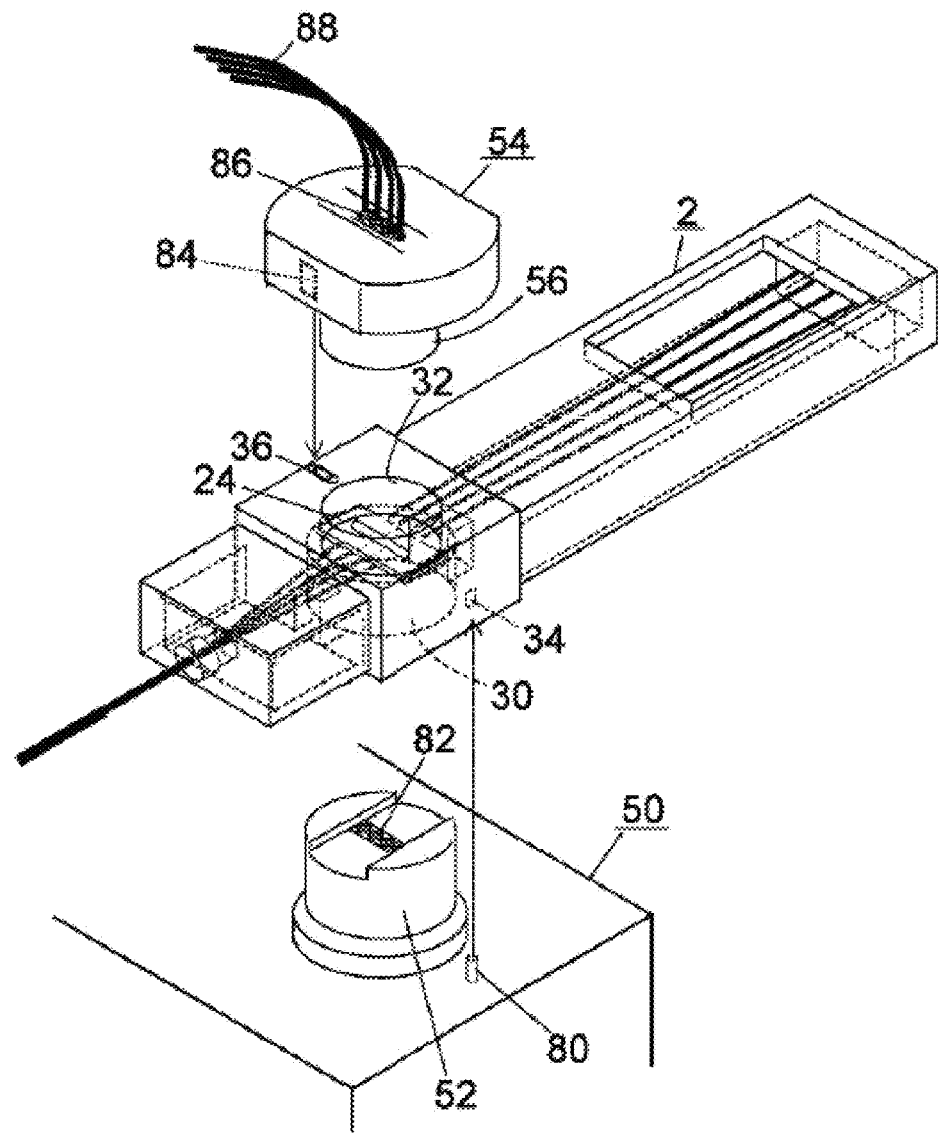
FIG. 6 is a perspective view showing a positioning part of a fluorescence-receiving unit and an excitation optical system unit positioned and fixed to the capillary cassette of one example of embodiment.

The positioning part of the fluorescence-receiving unit and the excitation optical system unit positioned and fixed to the capillary cassette 2 is shown in FIG. 6.

The position of the excitation optical system unit 50 is fixed to the mounting base 40. The excitation optical system unit 50 is equipped with a lens holder 52 at the end surface thereof and a pin 80 that regulates the direction of rotation. When the capillary cassette 2 is placed on the mounting base 40, the capillary cassette 2 is positioned to the excitation optical system unit 50 so that the lens holder 52 of the excitation optical system unit 50 is fitted into the positioning part 30 for the excitation optical system unit of the capillary cassette 2, and the pin 80 is inserted into the hole 34 for positioning of the back surface of the capillary cassette 2.

In the state where the capillary cassette 2 is positioned to the excitation optical system unit 50, in order to irradiate an excitation light to each capillary 14 in the capillary cassette 2, gradient index rod lenses (GRIN lenses) 82 are arranged at the lens holder 52 so as to face the detection window sections of the capillaries 14. The rod lenses 82 are arranged in a single tier corresponding to the array of the capillaries 14 in the detection area 10. The rod lens 82 has a lens outer diameter of 1.8 mm, for example, wherein the light condensed into a line shape from a light source is irradiated as a spot larger than the inner diameter of and smaller than the outer diameter of each capillary 14.

The fluorescence-receiving unit 54 is attached to the capillary cassette 2 from above the capillary cassette 2 in a state where the capillary cassette 2 is placed on the mounting base 40. The fluorescence-receiving unit 54 is equipped with a lens holder 56 at the end surface of the fluorescence-receiving unit 55 and a pin 84 that regulates the direction of rotation. When the fluorescence-receiving unit 54 is attached to the capillary cassette 2, the fluorescence-receiving unit 54 is positioned to the capillary cassette 2 so that the lens holder 56 of the fluorescence-receiving unit 54 is fitted into the positioning part 32 for the fluorescence-receiving unit of the capillary cassette 2, and the pin 84 is inserted into the hole 36 for positioning of the capillary cassette 2.

In order to receive the fluorescence emitted from the fluorescent substance that migrates inside each capillary 14 in the state where the capillary cassette 2 is placed on the mounting base 40, the gradient index rod lenses 86 are also arranged at the lens holder 56. The rod lenses 86 are also arranged in a single tier corresponding to the array of the capillaries 14 in the detection area 10. The rod lens 86 also has a lens outer diameter of 1.8 mm, for example, and receives the fluorescence from the capillaries 14 at the end of the rod lens 86. In order to transmit the fluorescence received by each rod lens 86 to an image element, the end surface of each optical fiber 88 is combined with the other end of the rod lens 86.

Spherical/aspherical lenses other than a refractive index distribution type may also be used as the rod lenses 82 and 86. A lens array can also be used in place of a rod lens.

Thus, it that the optic axes (medial axes) of the capillary array substrate 24 in the capillary cassette 2 and the upper and lower lens holders 52 and 56 are adjusted in advance so as to correspond to each other, and the direction of rotation of the lens holders 52 and 56 to the capillary cassette 2 is also regulated by the positioning pins 80 and 84; therefore, the arrangement of an excitation optical system unit and a fluorescence-receiving unit with respect to the capillaries 14 is completed simply by attaching the lens holders 52 and 56 mutually to the capillary cassette 2.

The method of analyzing a sample using the multicapillary electrophoresis device equipped with the capillary cassette 2 as shown in FIG. 5 will be described.

First, the capillaries 14 are filled up with an electrophoretic medium. The electrophoretic medium is press-fitted from an anode reservoir 70. Then, the tip of the flow path 64 is dipped in the cuvette 76 containing a sample, and the suction of the sample starts from the flow path 66 to the end 20 of the capillary 14. After the tip of the flow path 64 is immersed in the cuvette containing a buffer liquid, an electrode is inserted into the cuvette, and [the liquid in] the anode reservoir 70 is also exchanged to the buffer liquid, an electrode is also inserted in the anode reservoir 70, a voltage is applied between the two electrodes, and a sample is introduced into the end 20 of the capillary 14.

Thereafter, after the suction and the removal of the sample remained in the flow path 64 are carried out from the flow path 66, a voltage is applied between the two electrodes to perform electrophoresis and separation of the sample from the cathode side to the anode side of the capillary 14. In the detection area 10, an excitation light is irradiated from the excitation optical system unit 50 to the capillary 14, and the fluorescence emitted from the capillary 14 is received by the fluorescence-receiving unit 54 and transmitted to an image element to perform an image processing.

Figure 7:
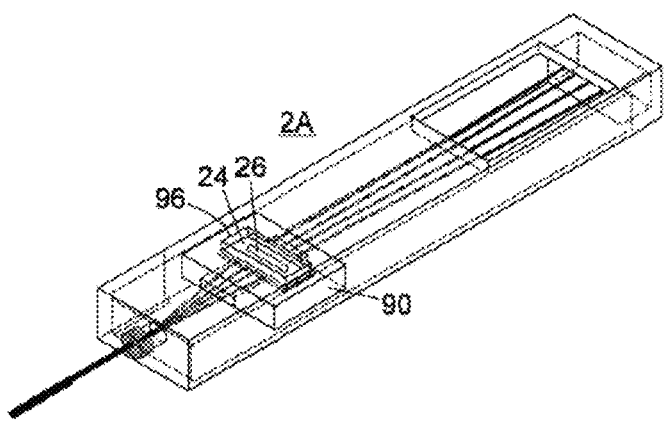
FIG. 7 is a perspective view showing the second example of embodiment of a capillary cassette.
Figure 8:
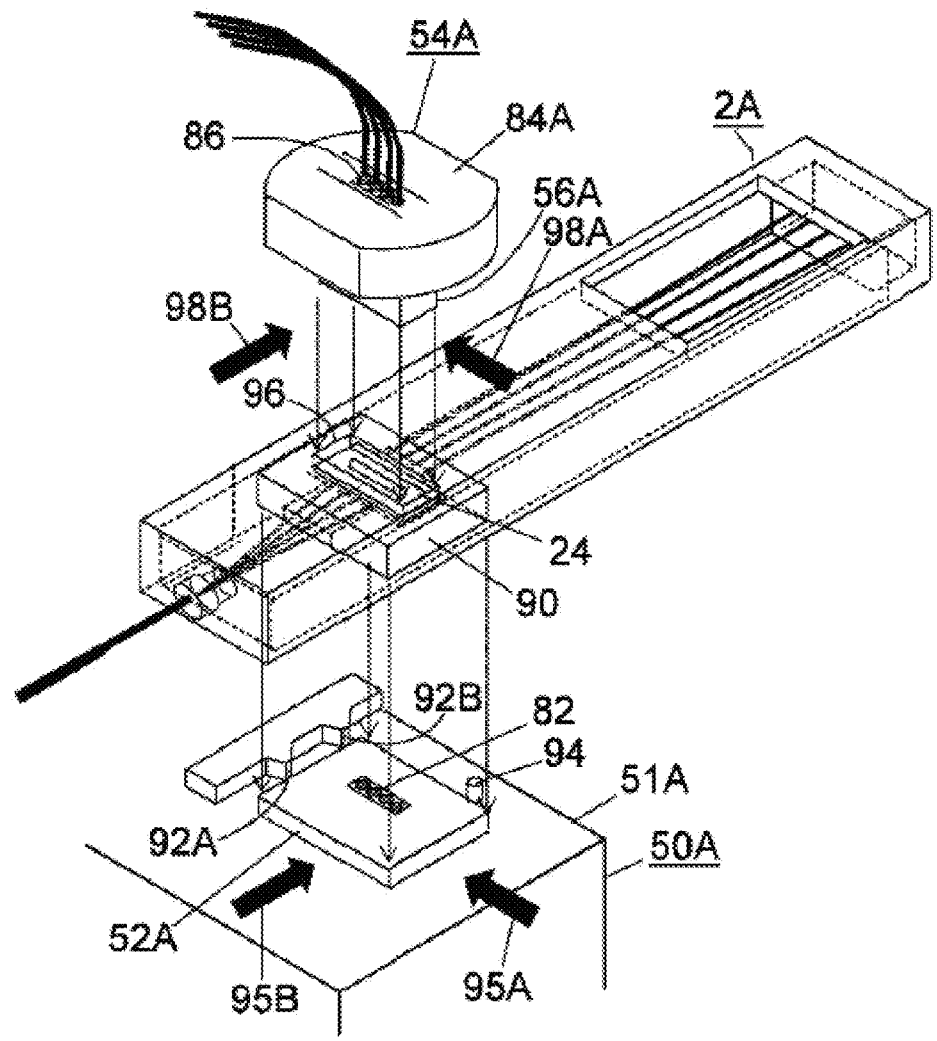
FIG. 8 is a perspective view showing a positioning part of a fluorescence-receiving unit and an excitation optical system unit positioned and fixed to the capillary cassette of the example of embodiment.

The second example of embodiment of a capillary cassette is shown in FIGS. 7 and 8. As opposed to the capillary cassette 2 of the first example of embodiment with the positioning by a pin that regulates the direction of rotation and the insertion in a cylindrical shape or a shape of truncated cone, the capillary cassette 2A of the second example of embodiment allows the positioning by a three-point support.

The capillary cassette 2A has an internal structure having an abutment surface parallel to a housing. This internal structure has a side surface 90 parallel to the medial axis of the capillary array substrate 24 as an abutment surface and serves as a positioning part for positioning to the excitation light irradiation section 51A of the excitation optical system unit 50A. The excitation light irradiation section 51A is equipped with two projections 92A and 92B along one direction used for positioning outside and at the end surface of the lens holder 52A holding the rod lenses 82, and one pin 94 arranged on the straight line that intersects perpendicularly to the straight line on which those projections 92A and 92B are arranged. When the capillary cassette 2A is mounted to a mounting device, the capillary cassette 2A is positioned to the excitation optical system unit 50A by allowing the projections 92A and 92B and the pin 94 to abut two side surfaces intersect perpendicularly to the abutment surface 90. In order to maintain the state of contact, the mounting device is provided with a mechanism, such as a spring, with which the capillary cassette 2A is pressed in the directions of arrows 95A and 95B, although the graphic display of the specific mechanism is omitted.

As a positioning part for positioning the fluorescence-receiving part 55A of the fluorescence-receiving unit 54A to the capillary cassette 2A, a rectangular opening 96 larger than the opening 26 of the capillary array substrate 24 is provided at the top surface side of the detector of the cassette housing 4. The lens holder 56A of the fluorescence-receiving part 55A holds the rod lenses 86 and has an outer shape in a rectangular parallelepiped shape inserted into the opening 96 of the positioning part.

To facilitate an easy operation of attaching and detaching the lens holder 56 to and from the opening 96A, the dimensions of the opening 96 can also be formed larger than the outer shape of the lens holder 56. In that case, in order to position the lens holder 56 to the two inner side surfaces intersect perpendicularly to the opening 96, the mounting device is provided with a mechanism, such as a spring, with which the fluorescence-receiving unit 54A is pressed in the directions of arrows 98A and 98B, although the graphic display of the specific mechanism is omitted.

The capillary cassette 2A of the second example of embodiment, as in the case with the capillary cassette 2 of the first example of embodiment, is also mounted to the mounting device as shown in FIG. 5 and constitutes a multicapillary electrophoresis device.

Figure 9:
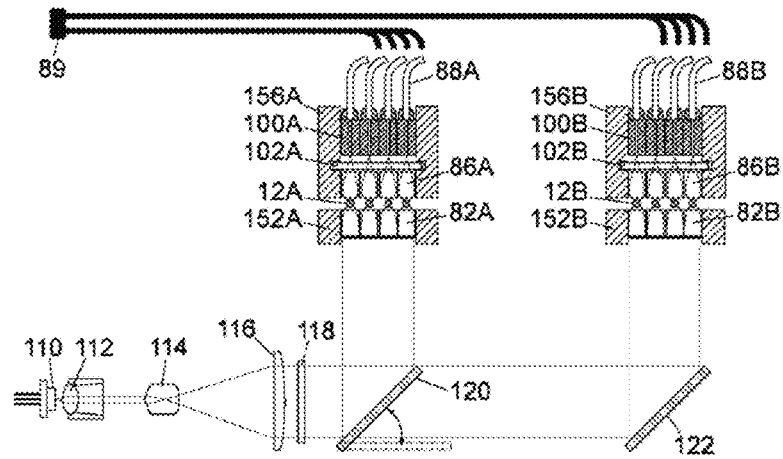
FIG. 9 is a cross sectional view illustrating a state where the excitation optical system and the fluorescence-receiving unit of another example of embodiment are cut in the direction along the capillary array of the capillary bundle.

Another example of embodiment of an excitation optical system and a fluorescence-receiving unit is shown in FIG. 9. FIG. 9 is a cross sectional view portraying a cut-away portion in the direction in alignment with the capillary array of the capillary bundle 12.

This example of embodiment, although the graphic display of the mounting device is omitted, has a configuration in which a plurality of capillary cassettes can be mounted. Although this example shows the case where two capillary cassettes are mounted, the number of the capillary cassettes mounted to a mounting device is not limited to two; it may be three or more.

In this example of embodiment, a group of the lens holder 152A of an excitation optical system unit and the lens holder 156A of a fluorescence-receiving unit is arranged to one of the capillary cassettes having a capillary bundle 12A, while a group of the lens holder 152B of an excitation optical system unit and the lens holder 156B of a fluorescence-receiving unit is arranged to the other capillary cassette having a capillary bundle 12B. The lens holder 152A and the lens holder 152B are the same as the lens holder 52 shown in FIG. 5, and the lens holder 156A and the lens holder 156B are the same as the lens holder 56 shown in FIG. 5.

The excitation optical system unit containing the lens holder 152A and the excitation optical system unit containing the lens holder 152B are provided with a common excitation light source 110. The excitation light source 110 is a laser diode (LD), for example.

A collimating lens 112 is arranged at the light-emitting side of the excitation light source 110 in order to convert the light from the excitation light source 110 into a parallel light flux, and a Powell lens 114 is arranged in order to convert the parallel light flux from the collimating lens 112 into a fan-shaped luminous light flux. A cylindrical lens 116 is arranged in order to convert a fan-shaped luminous light flux emitted from the Powell lens 114 into a strip-like parallel luminous flux. An excitation filter 118 is arranged, wherein this filter has wavelength characteristics so as to transmit a desired wavelength component used as an excitation light among the excitation lights converted into a strip-like parallel luminous light flux from the cylindrical lens 116 and remove the applicable wavelength component to the fluorescence to be detected. A movable mirror 120 and a fixed mirror 122 are arranged on the optical axis of the excitation light in order to irradiate the excitation light that penetrates through the excitation filter 118 to either the lens holder 152A or the lens holder 152B of an excitation optical system unit. The movable mirror 120 is disposed at a position at which the reflected excitation light is led to the lens holder 152A, and the fixed mirror 122 is disposed at a position at which the reflected excitation light is led to the lens holder 152B.

By the configuration of such an excitation optical system unit, the excitation light emitted from the common excitation light source 110 can be irradiated by switching to either the lens holder 152A or the lens holder 152B simply by switching the movable mirror 120.

The fluorescence received by the lens holder 156A and the lens holder 156B of the fluorescence-receiving unit is led to a detector from the introduction part 89 by the optical fibers 88A and 88B, respectively. A detector may adopted a configuration in which the fluorescence drawn from the introduction part 89 is dispersed with a spectroscope and detected by an image element. For example, this may be a case of determining a base sequence from a sample labelled with different fluorescent dyes to each base of four kinds of DNAs.

In this example of embodiment, an optical fiber array is reconstructed so that the optical fibers 88A and the optical fibers 88B may gather at a narrow pitch by the introduction part 89 to a detector. By adopting such configuration of the introduction part 89, an aberration due to an imperfect alignment in the spectroscope of a detector can be reduced.

EXPLANATIONS OF REFERENCES

2 Capillary cassette
10 Detection area
12, 12A, and 12B Capillary bundles
14 Capillary
24 Capillary array substrate
28 V groove
30, 32 Positioning parts
34 Hole for positioning
40 Mounting base
42 Lid
48 Temperature controller
46 Temperature sensor
44 Heater
50 Excitation optical system unit
51 51A Excitation light irradiation sections
52, 152A, and 152B Lens holders of an excitation optical system unit
54 Fluorescence-receiving unit
55 55A Fluorescence-receiving parts
56, 156A, and 156B Lens holders of a fluorescence-receiving unit
60 Cathode block
62 Flow path for sample suction or application of electrophoretic voltage
70 Anode reservoir
80 Pin for positioning
82 and 86 Rod lenses
88 Optical fiber
92A and for 92B Projections for positioning
94 Pin for positioning
102 Fluorescence filter
110 Excitation light source
120 Movable mirror
122 Fixed mirror

What is claimed is:

1. A capillary electrophoresis device, comprising:
a capillary cassette including an array substrate with an opening in which detection window sections of a plurality of capillaries are arranged, the capillary cassette includes an excitation-side positioning part and a fluorescence-side positioning part, the excitation-side positioning part and the fluorescence-side positioning part being provided on opposite sides of a detection window array;
a cassette loading device configured to mount the capillary cassette;
an excitation optical system unit provided with a positioning part positioned at the excitation-side positioning part of the capillary cassette attached to the cassette loading device and an excitation light irradiation section containing a rod-like lens array having the array corresponding to the detection window array so as to irradiate an excitation light to each of the detection window sections; and
a fluorescence-receiving unit equipped with a positioning part positioned at the fluorescence-side positioning part of the capillary cassette attached to the cassette loading device and a fluorescence-receiving unit containing a rod-like lens array having the array corresponding to the detection window array so as to receive the fluorescence from each of the detection window sections.

2. The capillary electrophoresis device as recited in claim 1, wherein the cassette loading device is equipped with a temperature control mechanism for adjusting the temperature of the capillaries in the capillary cassette attached.

3. The capillary electrophoresis device as recited in claim 1, wherein the fluorescence-receiving unit is provided with an optical fiber for each rod-like lens, wherein the optical fiber has an end surface for light incident at a position where a fluorescence from a rod-like lens of the fluorescence-receiving part is received and used for leading the fluorescence to a detector side.

4. The capillary electrophoresis device as recited in claim 3, wherein the end surface on the detector side of all optical fibers are gathered in a narrow region.

5. The capillary electrophoresis device as recited in claim 1, wherein a cathode block for connecting the tip of the capillary to a flow path for sample suction or application of electrophoretic voltage is provided in an end of the capillary cassette attached to the cassette loading device.

6. The capillary electrophoresis device as recited in claim 1, wherein the cassette loading device is configured to mount a plurality of the capillary cassettes,
the excitation optical system unit is provided with a common excitation light source, the excitation light irradiation section for each capillary cassette, and an optical-path switching mechanism for switching an optical path of the excitation light emitted from the common excitation light source and leading the excitation light to the excitation light irradiation section, and
the fluorescence-receiving unit is arranged for each capillary cassette.

7. The capillary electrophoresis device as recited in claim 1, wherein each rod-like lens of the rod-like lens array is a GRIN lens, a spherical/aspherical lens, or a lens array.

8. The capillary electrophoresis device as recited in claim 1, wherein the excitation optical system unit is provided with a Powell lens or an aspherical lens group arranged towards the direction in which the excitation light emitted from the excitation light source is converted to a line beam in alignment with the rod-like lens array.

9. A capillary cassette, in which detection window sections of a plurality of capillaries are arranged, the cassette comprising:
an excitation-side positioning part and a fluorescence-side positioning part, the excitation-side positioning part and the fluorescence-side positioning part being provided on opposite sides of a detection window array and attached to a capillary electrophoresis device; and
a cassette housing,
wherein the plurality of capillaries are arranged between one end and the other end of the cassette housing, and
wherein the cassette include an array substrate with a first opening.

10. The capillary cassette as recited in claim 9, wherein the excitation-side positioning part and the fluorescence-side positioning part of the capillary cassette each includes a second opening and a third opening corresponding to the shape of a lens holder of an excitation light irradiation section and a lens holder of a fluorescence-receiving unit respectively,
the excitation light irradiation section containing a rod-like lens array having an array corresponding to the detection window array so as to irradiate an excitation light to each of detection window sections, and
the fluorescence-receiving unit containing a rod-like lens array having an array corresponding to the detection window array so as to receive the fluorescence from each of detection window sections.

11. The capillary cassette as recited in claim 10, wherein the fluorescence-side positioning part and the excitation-side positioning part of the capillary cassette each contains an abutment surface positioned in contact with the fluorescence-receiving unit or the excitation light irradiation section.

12. The capillary cassette as recited in claim 9, wherein the cassette is provided with the array substrate including a section having grooves in a V-shape at equal intervals, wherein the arrangement of a detection window section is configured so that a plurality of capillaries are arranged one at a time in the grooves of the array substrate.

13. A capillary electrophoresis device, comprising:
a capillary cassette in which detection window sections of a plurality of capillaries are arranged, the capillary cassette includes an excitation-side positioning part and a fluorescence-side positioning part, the excitation-side positioning part and the fluorescence-side positioning part being provided on opposite sides of a detection window array,
a cassette loading device configured to mount the capillary cassette,
an excitation optical system unit provided with a positioning part positioned at the excitation-side positioning part of the capillary cassette attached to the cassette loading device and an excitation light irradiation section containing a rod-like lens array having the array corresponding to the detection window array so as to irradiate an excitation light to each of the detection window sections, and
a fluorescence-receiving unit equipped with a positioning part positioned at the fluorescence-side positioning part of the capillary cassette attached to the cassette loading device and a fluorescence-receiving unit containing a rod-like lens array having the array corresponding to the detection window array so as to receive the fluorescence from each of the detection window sections,
wherein the cassette loading device is further configured to mount a plurality of the capillary cassettes,
the excitation optical system unit is provided with a common excitation light source, the excitation light irradiation section for each capillary cassette, and an optical-path switching mechanism for switching an optical path of the excitation light emitted from the common excitation light source and leading the excitation light to the excitation light irradiation section, and
the fluorescence-receiving unit is arranged for each capillary cassette.

14. A capillary cassette, in which detection window sections of a plurality of capillaries are arranged, the cassette comprising:
an excitation-side positioning part and a fluorescence-side positioning part, the excitation-side positioning part and the fluorescence-side positioning part being provided on opposite sides of a detection window array and attached to a capillary electrophoresis device, and
a cassette housing,
wherein the plurality of capillaries are arranged between one end and the other end of the cassette housing, and
wherein the cassette further includes an array substrate including a section having grooves in a V-shape at equal intervals, the arrangement of a detection window section is configured so that a plurality of capillaries are arranged one at a time in the grooves of the array substrate.

* * * * *